US010662132B2

(12) United States Patent
Jo et al.

(10) Patent No.: US 10,662,132 B2
(45) Date of Patent: May 26, 2020

(54) METHOD FOR PREPARING ETHYLENE IN PROPYLENE PREPARATION PROCESS USING PROPANE DEHYDROGENATION REACTION

(71) Applicant: HYOSUNG CHEMICAL CORPORATION, Seoul (KR)

(72) Inventors: Bu Young Jo, Anyang-si (KR); Won Il Kim, Seongnam-si (KR); Tae Wan Kim, Ulsan (KR); Jong Chan Jang, Yeongcheon-si (KR); Young Gyo Choi, Seoul (KR); Jung Ill Cho, Ulsan (KR); Jong Ki Kim, Ulsan (KR)

(73) Assignee: HYOSUNG CHEMICAL CORPORATION, Seoul (KR)

( * ) Notice: Subject to any disclaimer, the term of this patent is extended or adjusted under 35 U.S.C. 154(b) by 0 days.

(21) Appl. No.: 16/331,350

(22) PCT Filed: Jun. 26, 2017

(86) PCT No.: PCT/KR2017/006694
§ 371 (c)(1),
(2) Date: Mar. 7, 2019

(87) PCT Pub. No.: WO2018/048073
PCT Pub. Date: Mar. 15, 2018

(65) Prior Publication Data
US 2019/0194094 A1    Jun. 27, 2019

(30) Foreign Application Priority Data

Sep. 9, 2016    (KR) .................. 10-2016-0116791

(51) Int. Cl.
*C07C 7/00*    (2006.01)
*C07C 7/09*    (2006.01)
(Continued)

(52) U.S. Cl.
CPC ............... *C07C 7/005* (2013.01); *C07C 4/06* (2013.01); *C07C 5/333* (2013.01); *C07C 7/00* (2013.01);
(Continued)

(58) Field of Classification Search
None
See application file for complete search history.

(56) References Cited

U.S. PATENT DOCUMENTS 3,445,541 A * 5/1969 Heckelsberg ......... C07C 5/3332
585/630
4,368,061 A    1/1983 Mestrallet et al.
(Continued)

FOREIGN PATENT DOCUMENTS

KR       10-0230672      11/1999
KR    10-2007-0093445     9/2007
(Continued)

OTHER PUBLICATIONS

International Search Report, issued in the corresponding PCT application No. PCT/KR2017/006694, dated Oct. 31, 2017, 7 pages.

*Primary Examiner* — Philip Y Louie
(74) *Attorney, Agent, or Firm* — Hamre, Schumann, Mueller & Larson, P.C.

(57) ABSTRACT

The present invention relates to a method of producing ethylene by separately collecting ethane and ethylene which are by-products of a propylene preparation process using propane dehydrogenation reaction and also combining an existing propylene preparation process with a process of converting ethane to ethylene. According to the present invention, valuable ethylene may be produced by converting most of ethane and ethylene, i.e., by-products of a propane dehydrogenation process, into ethylene without using the ethane as fuel, thereby improving process economic efficiency. Furthermore, a product line in the process of propane (Continued)

dehydrogenation reaction may be changed from a propylene product alone into two products, i.e., propylene and ethylene, and thus the operating conditions of a propylene dehydrogenation reactor and the operating conditions of a de-ethanizer may be adjusted according to the market situation, thereby increasing the production proportion of a favorable product line.

10 Claims, 2 Drawing Sheets

(51) Int. Cl.
 *C07C 11/04* (2006.01)
 *C07C 4/06* (2006.01)
 *C07C 5/333* (2006.01)
(52) U.S. Cl.
 CPC .............. *C07C 7/09* (2013.01); *C07C 11/04* (2013.01); *Y02P 20/582* (2015.11)

(56) References Cited

U.S. PATENT DOCUMENTS

| | | | | |
|---|---|---|---|---|
| 4,458,096 | A | * 7/1984 | Phillips | ............... C07C 11/04 585/302 |
| 5,220,097 | A | 6/1993 | Lam et al. | |
| 5,457,256 | A | * 10/1995 | Mitariten | ............... C07C 5/333 585/655 |
| 2012/0302807 | A1 | * 11/2012 | Elseviers | ............... C10G 25/03 585/315 |
| 2014/0323791 | A1 | 10/2014 | Das et al. | |

FOREIGN PATENT DOCUMENTS

| | | |
|---|---|---|
| KR | 10-2008-0036960 | 4/2008 |
| KR | 10-2014-0048951 | 4/2014 |

\* cited by examiner

METHOD FOR PREPARING ETHYLENE IN PROPYLENE PREPARATION PROCESS USING PROPANE DEHYDROGENATION REACTION

TECHNICAL FIELD

The present invention relates to a method for preparing ethylene in a propylene preparation process using propane dehydrogenation reaction, and more particularly to a method of producing valuable ethylene by separately collecting ethane and ethylene which are by-products of a propylene preparation process using propane dehydrogenation reaction and also combining an existing propylene preparation process with a process of converting ethane to ethylene.

BACKGROUND ART

Propane dehydrogenation reaction is a process of producing propylene by removing some hydrogen atoms from propane through a chemical reaction. The reaction of dehydrogenation of propane to propylene produces olefins, which are more reactive than alkane feedstocks and easily form coke, at high temperatures used for dehydrogenation. This process is based on an endothermic reaction ($\Delta H_0^{298}$=+124 kJ/mole), and produces methane, ethane, ethylene, and the like through side reactions.

Of these, ethylene has recently shown an increasing demand in the chemical raw material market. In the past, ethylene was produced chiefly as a by-product of an olefin preparation process, particularly a propylene preparation process. An existing propane dehydrogenation process is a process that removes by-products (methane, ethane, and ethylene) via a de-ethanizer configured to separate C2 and compounds lighter than C2 after propane dehydrogenation reaction, separates the final product propylene from unreacted propane via a propane/propylene splitter, and recycles the unreacted propane for the reaction. In this case, the by-products (methane, ethane, and ethylene) which are separated in the de-ethanizer are recycled as fuel for a heating furnace. However, using valuable ethylene only as fuel is a great economic loss. Furthermore, this supply system alone cannot meet the current demand for ethylene.

DISCLOSURE

Technical Problem

The present invention has been conceived to overcome the above-described problems, and an object of the present invention is to provide a method for preparing valuable ethylene by collecting ethane and ethylene discharged out of a system in a propane dehydrogenation process and then converting the ethane to ethylene.

Technical Solution

An aspect of the present invention for achieving the above object is directed to a method for preparing ethylene in a propylene preparation process using a propane dehydrogenation process, the method including the steps of: passing a product stream containing methane, ethane, and ethylene, which are by-products generated in a de-ethanizer in a propane dehydrogenation process, through a demethanizer, thereby preferentially separating the methane; separating the ethane from the ethylene by passing the reactant stream, from which the methane has been separated, through an ethane/ethylene splitter; converting the ethane to ethylene by additionally allowing the separated ethane to react in an ethane reactor; passing the reactant stream, which has passed through the ethane reactor, through a quenching tower, thereby cooling it; neutralizing the cooled reactant stream by passing it through a scrubber; and introducing the neutralized reactant stream in front of a compressor, and recycling it to the dehydrogenation process; wherein the ethylene is recovered in the step of separating the ethane from the ethylene and the step of converting the ethane to the ethylene.

Advantageous Effects

According to the method for preparing ethylene using a propane dehydrogenation process according to the present invention, valuable ethylene may be produced by converting most of ethane and ethylene, i.e., by-products of the propane dehydrogenation process, into ethylene without using the ethane as fuel, thereby improving process economic efficiency. Furthermore, a product line in the process of propane dehydrogenation reaction may be changed from a propylene product alone into two products, i.e., propylene and ethylene, and thus the operating conditions of a propylene dehydrogenation reactor and the operating conditions of a de-ethanizer may be adjusted according to the market situation, thereby increasing the production proportion of a favorable product line.

BEST MODE

Figure 1:
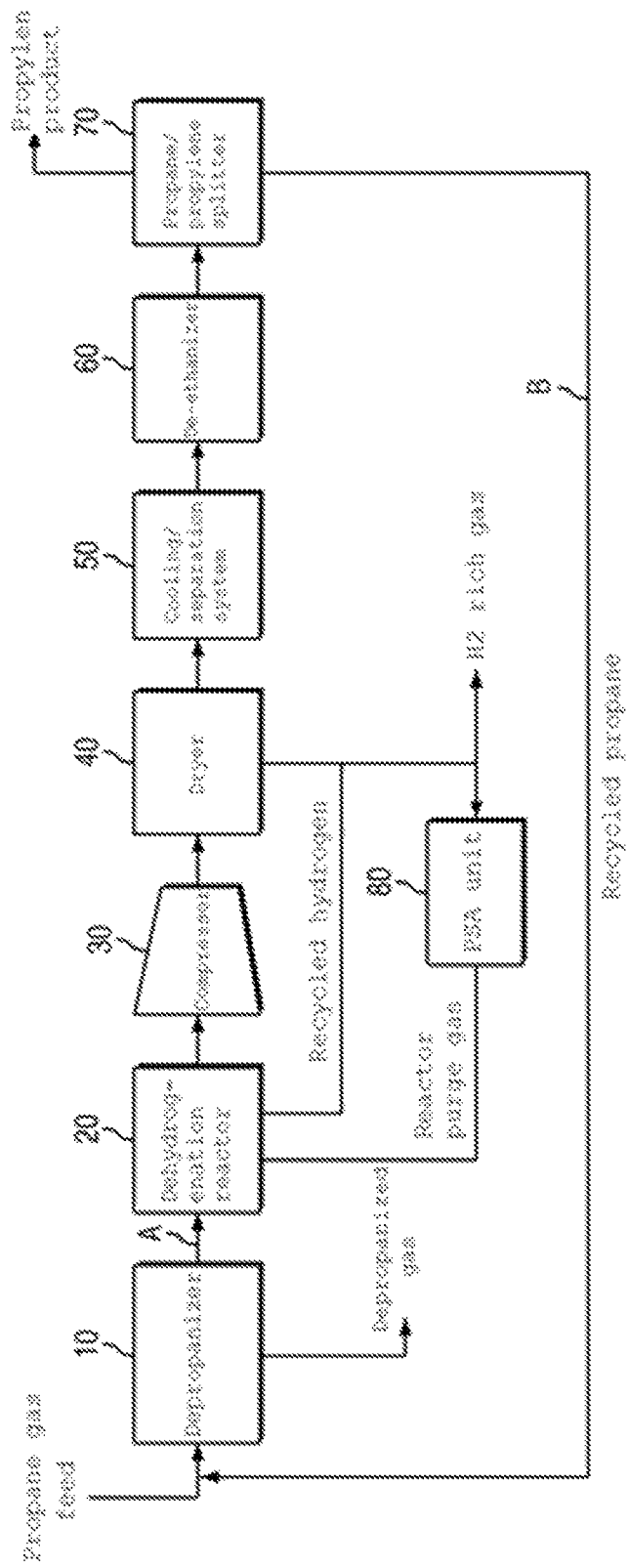
FIG. 1 is a process flow chart schematically showing a process of preparing propylene from a hydrocarbon mixture according to a conventional art.

The present invention will be described in greater detail below with reference to the accompanying drawings. Although common terms which are widely used currently have been selected as terms used in the present invention, a term selected by the applicant as desired may be used in a particular case. In this case, the meaning of the term should be understood by taking into account the meaning described or used in the detailed description of the invention rather than the simple name of the term. Throughout the specification, like reference symbols denote like components.

Although the accompanying drawings describe specific steps of the dehydrogenation process of the present invention, this dehydrogenation process may have various process steps which are performed in a particular application and are suitable for a particular environment, and the broad application of the present invention is not limited to the specific embodiments to be described below. Furthermore, the numbers in the drawings represent a simple schematic view of the dehydrogenation process of the present invention, and only main components are shown in the drawings. In addition, pumps, moving pipes, valves, hatches, access outlets, and other similar components are omitted in the drawings.

Using these components to modify the reaction apparatus used in the described dehydrogenation process is known to those skilled in the art, and does not depart from the scope and spirit of the appended claims.

The term "reactant stream" used herein refers to a reaction product produced through a dehydrogenation reaction. It refers to a gas, a liquid, a gas or liquid containing a dispersed solid, or a mixture thereof which may contain hydrogen, propane, propylene, ethane, ethylene, methane, butane, butylene, butadiene, nitrogen, oxygen, vapor, carbon monoxide, carbon dioxide, or the like.

The term "reactor" used herein refers to a reaction apparatus in which reactant gases come into contact with a catalyst on a catalyst bed.

The use of the terms "lower," "downward," "upper," and "upward" used herein is based on the direction of gravity.

The numbers in the drawings represent a simple schematic view of the dehydrogenation process according to the present invention, and only main components are shown in the drawings.

FIG. 1 is a process flow chart schematically showing a process of preparing propylene from a hydrocarbon mixture according to a conventional art. Referring to FIG. 1, propane and hydrogen, which are reactant gases, are introduced into a catalyst-filled dehydrogenation reactor 20, and are subjected to propane dehydrogenation reaction. In front of the dehydrogenation reactor 20 in which propane dehydrogenation reaction occurs, there may be further included a depropanizer 10 configured to remove butane, butylene, butadiene, and the like, i.e., compounds that cause the production of coke through polymerization on the catalyst located inside the reactor, before the components contained in the reactant gases are introduced into the dehydrogenation reactor 20. The reactant gases other than hydrogen are liquefied by compressing the dehydrogenated reactant stream in a compressor 30, and then impurities, such as water, hydrogen chloride, and hydrogen sulfide, are removed in a dryer 40. The reactant stream from which the impurities have been removed is further liquefied by compression in a cooling/separation system 50. The liquefied reactant stream is separated by a column in a de-ethanizer 60 to thus remove methane, ethane, and ethylene, i.e., by-products, and the remaining reactant stream is fed into a propane/propylene splitter 70. The reactant stream fed into the propane/propylene splitter 70 also contains butane, butylene, and butadiene, which are by-products. Unreacted propane, butane, and butylene are separated by a column, and only a pure propylene product is recovered.

In the above-described process, a process of separately collecting a hydrogen gas from the reactant stream having passed through the dryer 40 and increasing the purity of the hydrogen gas in a PSA (Pressure Swing Adsorption) unit 80 is separately performed. The hydrogen gas with increased purity may be sold commercially, and a portion thereof is transferred to the dehydrogenation reactor 20 and recycled as a reactant gas.

Unreacted propane separated in the propane/propylene splitter 70 is transferred to a location in front of the depropanizer 10 through a propane recycling pipe B and recycled as a feed propane gas.

Figure 2:
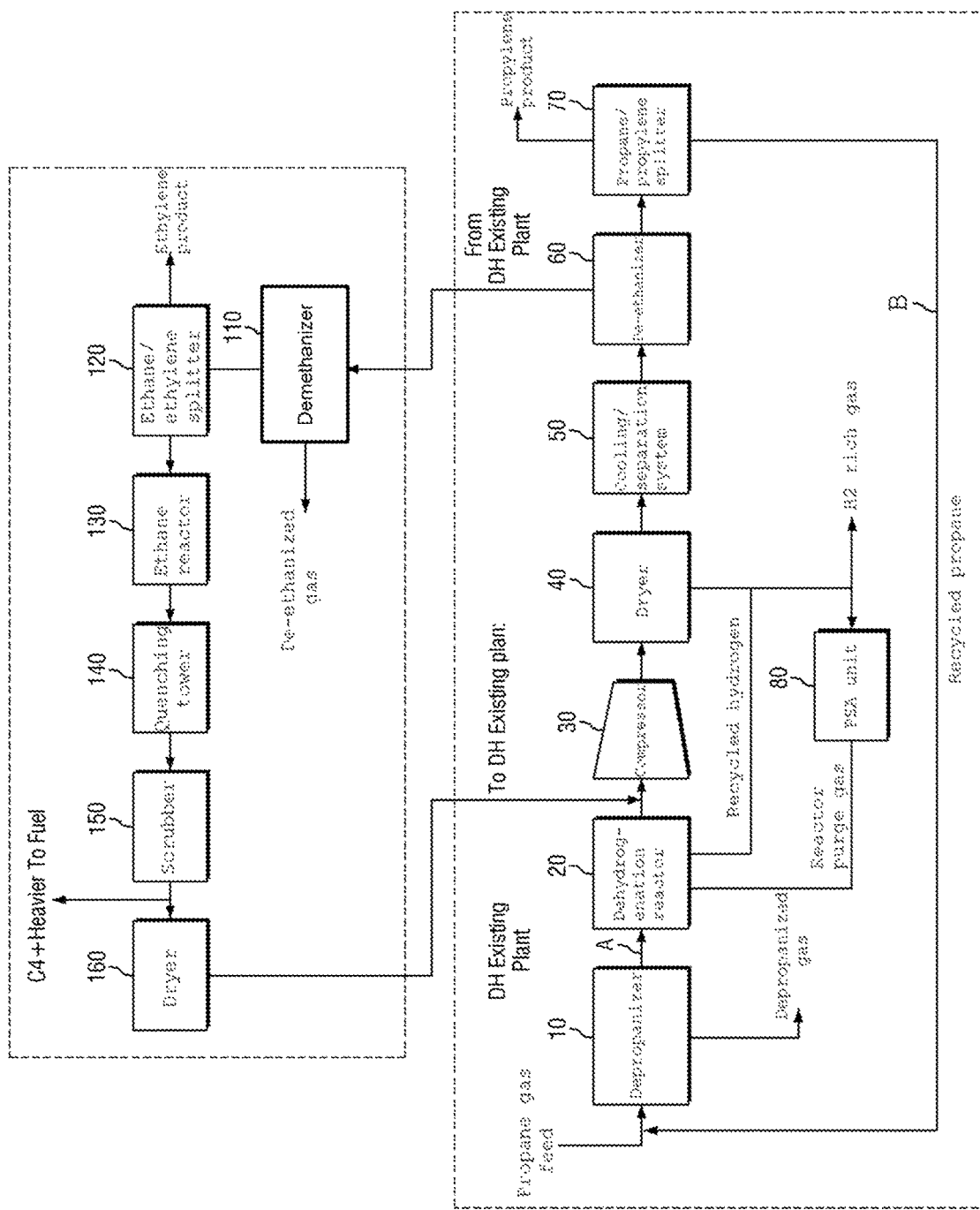
FIG. 2 is a process flow chart schematically showing a process of preparing ethylene from a hydrocarbon mixture in a propylene preparation process using propane dehydrogenation reaction according to an embodiment of the present invention.

FIG. 2 is a process flow chart schematically showing a process of preparing ethylene from a hydrocarbon mixture in a propylene preparation process using propane dehydrogenation reaction according to an embodiment of the present invention. Referring to FIG. 2, a propane dehydrogenation process system for performing an ethylene preparation method using propane dehydrogenation reaction may include an individual pipeline A which is configured to introduce propane and hydrogen reactant gases into a reactor 20, or may include a plurality of individual pipelines (not shown) which are branched off from a single pipeline connected directly to the reactor and into which the components contained in the reactant gases are individually introduced. Through this plurality of individual pipelines, reactant gases containing one or more of vapor, carbon monoxide, and carbon dioxide may be introduced.

In one embodiment of the present invention, the reactor 20 is not particularly limited as long as it can perform the dehydrogenation reaction. For example, it may be a tubular reactor, a tank reactor, or a fluidized bed reactor. As another example, the reactor may also be a fixed-bed reactor, and a fixed-bed multitubular reactor or plate-type reactor.

Propane and hydrogen, which are reactant gases, pass through a depropanizer 10, and are introduced into a catalyst-filled dehydrogenation reactor 20 in which they are subjected to propane dehydrogenation reaction. In the depropanizer 10 disposed in front of the dehydrogenation reactor 20 in which propane dehydrogenation reaction occurs, butane, butylene, butadiene, and the like, which are compounds that cause the production of coke through polymerization on the catalyst located inside the reactor, are removed before the components contained in the reactant gases are introduced into the dehydrogenation reactor 20. Thereafter, the reactant gases other than hydrogen gas are liquefied by compressing the dehydrogenized reaction reactant stream in a compressor 30. Thereafter, in a dryer 40 configured to remove water and impurities from the reaction product, impurities, such as water, hydrogen chloride, and hydrogen sulfide, are removed by drying.

The reactant stream from which the impurities have been removed in the dryer 40 is further liquefied by compression in a cooling/separation system 50. The cooling/separation system 50 may include a heat removing device (not shown) configured to remove additional heat generated during compression so that operation in a subsequent de-ethanizer 60 is possible. The heat removing device can also remove heat through heat exchange with a low-temperature gas or liquid reaction product, such as the hydrogen gas recycled from the dryer 40, the liquefied propane separated in the depropanizer 10, or the like. The liquefied reaction stream is separated in a de-ethanizer 60, and methane, ethane, and ethylene, which are by-products, are introduced into a demethanizer 110. The remaining reactant stream from which the by-products have been removed is introduced into a propane/propylene splitter 70. Unreacted propane, butane, and butylene in the reactant stream introduced into the propane/propylene splitter 70 are separated by a column, and a pure propylene product is recovered.

The separated unreacted propane is fed to a location in front of the dehydrogenation reactor 20 through a propane recycling pipeline B, i.e., an inert recycle line, and is recycled as a feed propane gas. In this case, a process of separately collecting a hydrogen gas from the reactant stream having passed through the dryer 40 and then increasing the purity of the hydrogen gas in a PSA unit 80 may be separately performed. The hydrogen gas with increased purity is sold commercially, or is transferred to the dehydrogenation reactor 20 and recycled as a reactant gas. The unreacted propane separated in the propane/propylene splitter 70 is transferred to a location in front of the depropanizer 10 through a propane recycling pipe B, and is recycled as a feed propane gas.

The method for preparing ethylene in a propylene dehydrogenation process according to the present invention includes the steps of: passing a reactant stream containing methane, ethane, and ethylene, which are by-products generated in a de-ethanizer 60, through a demethanizer 110, thereby preferentially separating the methane; passing the reactant stream, from which the methane has been separated, through an ethane/ethylene splitter 120, thereby separating the ethane from the ethylene; additionally allowing the separated ethane to react in an ethane reactor 130, thereby converting the ethane to ethylene; passing the reactant stream, which has passed through the ethane reactor 130, through a quenching tower 140, thereby cooling the reactant stream; and neutralizing the cooled reactant stream by passing it through a scrubber 150, wherein the neutralized reactant stream is continuously recycled to the dehydrogenation process by introducing it between the reactor 20 of the existing dehydrogenation catalytic reaction process and the main compressor 30. The method may further include, after the neutralizing step, the step of removing impurities, such as water, hydrogen chloride, and hydrogen sulfide, through drying in the dryer 160.

In other words, the ethylene preparation process according to the present invention is configured such that ethylene produced in the ethane reactor 130 after passage through the de-ethanizer 60, the demethanizer 110, and the ethane/ethylene splitter 120 is separated again. Ethane collected after passage through the ethane/ethylene separator 120 may additionally be reacted in the ethane reactor 130, and thus the ethane separated after propane dehydrogenation reaction may be converted into ethylene, thereby producing additional ethylene.

The individual process steps of the method for preparing ethylene in a propane dehydrogenation process will be described in detail below with reference to examples. However, these examples should not be considered to restrict or limit the present invention.

a) Step of Preferentially Separating Methane

A reaction stream having passed through the de-ethanizer 60 contains methane, ethane, and ethylene as reaction by-products. These reaction by-products are passed through the demethanizer 110, and the methane is preferentially separated by a column. The process conditions are a temperature of −129° C. to 52° C. and a pressure of 5 kgf/cm$^2$ to 50 kgf/cm$^2$. Table 1 below shows process conditions for a gas which is introduced into the demethanizer 110. The composition of the gas which is introduced into the demethanizer 110 may vary depending on the operating conditions of the process and the amount of propylene produced.

TABLE 1

| Item | | Value |
|---|---|---|
| Bottom layer conditions | Pressure [kgf/cm$^2$_g] | 0.4 to 8 |
| | Temperature [° C.] | −20 to 80 |
| | Composition | |
| Methane | [Mol %] | 16.7 |
| Ethane | | 75.8 |
| Ethylene | | 6.2 |
| Hydrogen | | 1.2 |

The temperature of the preferentially separated methane gas is, for example, 40° C., and the pressure thereof is, for example, 3.2 kgf/cm$^2$. The separated methane may be used as heating fuel.

b) Step of Separating Ethane from Ethylene

The reactant stream from which the methane has been separated is immediately passed through the ethane/ethylene splitter 120, thereby separating the ethane from the ethylene. The process conditions are a temperature of −60° C. to 40° C. and a pressure of 10 kgf/cm$^2$ to 80 kgf/cm$^2$.

For example, the temperature of the separated ethylene gas is 25° C., and the pressure thereof is 40 kgf/cm$^2$.

c) Step of Converting Ethane to Ethylene

The ethane separated in step b) is additionally allowed to react in the ethane reactor 130, thereby converting the ethane to ethylene. The reaction that converts the ethane to ethylene in the ethane reactor 130 does not particularly require a catalyst. Alternatively, the ethane may also be converted into ethylene in the presence of a catalyst, and the catalyst used in this case is not particularly limited. For example, the catalyst may be a platinum catalyst. Process conditions for the ethane reactor 130 is a reaction temperature of 650° C. to 950° C. and a pressure of 0.1 kgf/cm$^2$ to 10 kgf/cm$^2$.

In one example, the temperature of the ethane gas which is introduced into the ethane reactor 130 may be −30° C., and the pressure thereof may be 1.2 kgf/cm$^2$. In addition, immediately in front of the ethane reactor 130, there may be provided a heater (not shown) configured to supply heat necessary for a reaction occurring in the ethane reactor 130. Furthermore, in front of the ethane reactor 130, an additional gas supply line configured to supply propane may be disposed and adjust the ratio of the amount of ethylene produced to the amount of propylene produced.

d) Cooling Step

The reactant stream the temperature of which has been increased by the ethane-to-ethylene conversion reaction in the ethane reactor 130 is cooled in the quenching tower 140. The reaction product obtained from the ethane reactor 130 may be in the form of high-temperature gas, and accordingly needs to be cooled before being supplied again to the main dehydrogenation process apparatus. A cooling method which is used in the cooling step is not particularly limited. For example, there may be used a cooling method in which the reaction product is brought into direct contact with a cooling solvent, or there may be also used a cooling method in which the reaction product is brought into indirect contact with a cooling solvent.

e) Neutralization Step

The cooled reactant stream is passed through the scrubber 150, thereby neutralizing the catalyst and additional gases.

f) Drying Step

The neutralized reactant stream is passed through the dyer 160, thereby removing impurities, such as water, hydrogen chloride, and hydrogen sulfide. The process conditions are a temperature of −40° C. to 100° C. and a pressure of 0.01 kgf/cm$^2$ to 60 kgf/cm$^2$.

After the neutralization step e) or drying step f), the reactant stream is introduced between the dehydrogenation reactor 20 in the existing dehydrogenation catalytic reaction process and the compressor 30. The reactant stream which is introduced in front of the compressor 30 contains propane, propylene, ethane, ethylene, methane, and hydrogen gases. In one example, the temperature of the reactant stream is 30° C., and the pressure thereof may be 0.1 kgf/cm$^2$.

According to the present invention, the ethane reactor 130 is disposed behind the ethane/ethylene splitter 120, and thus the concentration of ethylene which is introduced into the de-ethanizer 60 during recycling preparation increases. Accordingly, the produced ethylene may be preferentially separated, thereby preventing catalyst coking in the ethane reactor 130 and also preventing ethylene from being lost by ethylene side reactions. Furthermore, since ethylene having passed through the ethane/ethylene splitter 120 and ethylene produced in the ethane reactor 130 are separated again, valuable ethylene may be produced by converting most ethane, i.e., a by-product of the propane dehydrogenation process, into ethylene without using the ethane as cheap fuel, thereby improving process economic efficiency. Accordingly, a product line in the process of propane dehydrogenation reaction may be changed from a propylene product alone to two products, i.e., propylene and ethylene, and thus the operating conditions of the propylene dehydrogenation reactor and the operating conditions of the de-ethanizer may be adjusted according to the market situation.

While the present invention has been described in connection with various specific embodiments, it should be understood that various modifications thereof will become apparent to a person skilled in the art who has read the specification. Therefore, the invention described herein is intended to embrace such modifications as falling within the scope of the appended claims.

The invention claimed is:

1. A method for preparing ethylene in a propylene preparation process, comprising:
    obtaining a first reactant stream containing methane, ethane, and ethylene from a de-ethanizer disposed downstream of a compressor in a propane dehydrogenation process;
    passing the first reactant stream through a demethanizer to separate methane from the first reactant stream and obtain a methane stream and a second reactant stream comprising ethane and ethylene;
    passing the second reactant stream through an ethane/ethylene splitter to obtain an ethylene product and a third reactant stream containing ethane;
    passing the third reactant stream through an ethane reactor to convert ethane to ethylene and obtain a fourth reactant stream comprising ethylene;
    passing the fourth reactant stream through a quenching tower to cool the fourth reactant stream and obtain a cooled reactant stream;
    passing the cooled reactant stream through a scrubber to obtain a neutralized reactant stream; and
    introducing the neutralized reactant stream to the compressor that is disposed downstream of a catalyst-filled dehydrogenation reactor in the propane dehydrogenation process.

2. The method of claim 1, further comprising drying the neutralized reactant stream in a dryer to remove impurities.

3. The method of claim 1, wherein the propane dehydrogenation process comprises:
    introducing propane and hydrogen into the catalyst-filled dehydrogenation reactor and performing propane dehydrogenation in the catalyst-filled dehydrogenation reactor to obtain a dehydrogenated reactant stream;
    compressing and liquefying the dehydrogenated reactant stream in the compressor to obtain a hydrogen gas and a liquefied reactant stream;
    passing the liquefied reactant stream through a dryer to remove impurities to obtain a purified reactant stream;
    passing the purified reactant stream through a cooling/separation system to further liquefy and obtain a second liquefied reactant stream;
    passing the second liquefied reactant stream through the de-ethanizer to obtain the first reactant stream and a de-ethanized reactant stream containing propane and propylene; and
    introducing the de-ethanized reactant stream into a propane/propylene splitter to obtain unreacted propane and a propylene product.

4. The method of claim 3, further comprising separately collecting the hydrogen gas, increasing purity of the hydrogen gas in a PSA unit, and then recovering the hydrogen gas.

5. The method of claim 3, wherein the unreacted propane separated in the propane/propylene splitter is re-introduced into the catalyst-filled dehydrogenation reactor through a propane recycling pipe.

6. The method of claim 3, wherein the cooling/separation system includes a heat removing device configured to remove heat generated during compression.

7. The method of claim 1, wherein the methane stream has a temperature of −20° C. to 80° C. and a pressure of 0.4 kgf/cm$^2$ to 8 kgf/cm$^2$.

8. The method of claim 1, wherein the ethane reactor is provided with a heater to supply heat for a reaction in the ethane reactor.

9. The method of claim 1, wherein process conditions of the ethane reactor include a reaction temperature of 650° C. to 950° C. and a pressure of 0.1 kgf/cm$^2$ to 10 kgf/cm$^2$.

10. The method of claim 1, wherein the ethane reactor is provided with a separate gas supply line, and propane is supplied through the gas supply line to adjust a ratio of an amount of ethylene produced to an amount of propylene produced.

* * * * *